United States Patent
Lindmark

(10) Patent No.: US 8,228,139 B2
(45) Date of Patent: *Jul. 24, 2012

(54) TRANSMISSION LINE COMPRISED OF A CENTER CONDUCTOR ON A PRINTED CIRCUIT BOARD DISPOSED WITHIN A GROOVE

(75) Inventor: Björn Lindmark, Sollentuna (SE)

(73) Assignee: Powerwave Technologies Sweden AB, Kista (SE)

( * ) Notice: Subject to any disclaimer, the term of this patent is extended or adjusted under 35 U.S.C. 154(b) by 255 days.

This patent is subject to a terminal disclaimer.

(21) Appl. No.: 12/406,839

(22) Filed: Mar. 18, 2009

(65) Prior Publication Data

US 2009/0243763 A1 Oct. 1, 2009

Related U.S. Application Data

(60) Provisional application No. 61/037,986, filed on Mar. 19, 2008.

(51) Int. Cl.
  *H01P 5/12* (2006.01)
  *H01P 3/08* (2006.01)
(52) U.S. Cl. .......... 333/136; 333/238; 333/246
(58) Field of Classification Search .......... 333/238, 333/246, 128, 136
See application file for complete search history.

(56) References Cited

U.S. PATENT DOCUMENTS

| | | | |
|---|---|---|---|
| 3,192,492 A | 6/1965 | Linder | |
| 3,496,492 A | 2/1970 | Kurzl | |
| 3,518,579 A * | 6/1970 | Hoffman | 333/21 R |
| 3,863,181 A * | 1/1975 | Glance et al. | 333/243 |
| 3,904,997 A | 9/1975 | Stinehelfer, Sr. | |
| 4,254,383 A | 3/1981 | Wolfe | |
| 4,365,222 A | 12/1982 | Lampert | |
| 4,437,074 A | 3/1984 | Cohen et al. | |
| 4,575,700 A | 3/1986 | Dalman | |
| 5,304,959 A | 4/1994 | Wisherd et al. | |
| 5,319,329 A * | 6/1994 | Shiau et al. | 333/204 |
| 5,652,557 A | 7/1997 | Ishikawa | |
| 2002/0080086 A1 | 6/2002 | Webb | |
| 2002/0130739 A1 | 9/2002 | Cotton | |

(Continued)

FOREIGN PATENT DOCUMENTS

DE 935014 11/1955

(Continued)

OTHER PUBLICATIONS

Office Action (Communication pursuant to Article 94(3) EPC) pertaining to European Application No. 09 445 008.7 dated Mar. 12, 2010.

(Continued)

*Primary Examiner* — Benny Lee
(74) *Attorney, Agent, or Firm* — OC Patent Law Group

(57) ABSTRACT

The invention relates to a transmission line (1) comprising:
  a groove (2) defined by two parallel conducting walls (3) and a conducting floor (4) all electrically connected to each other, together forming a peripheral conductor of the transmission line, and
  a center conductor (5), at least partly submersed in the groove (2), the center conductor (5) being isolated from the conducting walls (3) and the conducting floor (4) of the groove (2). The transmission line is distinguished in that the center conductor (5) comprises at least one conductor formed on a side of a printed circuit board (6). The invention also relates to a method for the production of a transmission line.

12 Claims, 7 Drawing Sheets

U.S. PATENT DOCUMENTS

2005/0190019 A1  9/2005  Metz

FOREIGN PATENT DOCUMENTS

| | | |
|---|---|---|
| JP | 01 125101 | 5/1989 |
| JP | 02 1113702 | 4/1990 |
| WO | 2007/036607 | 4/2007 |

OTHER PUBLICATIONS

Nicholas Tomcia, "The Characteristic Impedance of a Transmission Line Consisting of a Ribbon in a Rectangular Trough," Thesis in partial fulfillment for the degree of Master of Applied Science, Department of Electrical Engineering, University of Toronto, Ontario, Canada, Oct. 1954.

Wenzhang Wang et al., "Static Analysis of Millimeter Wave Transmission Lines Micromachined in Silicon Substrate," Digest of the Antennas and Propagation Society International Symposium, Seattle, WA, Jun. 19-24, 1994, New York, US, vol. 3, Jun. 20, 1994, pp. 1960-1963, XP010142433, ISBN:978-0-7803-2009-3.

International Type Search Report for SE National Application No. 0800642-1 dated Sep. 3, 2008.

Extended European Search Report pertaining to European Application 09445008.—dated Jun. 24, 2009.

Wadell, Brian C., "Transmission Line Design Handbook," Artech House, 1991, p. 63.

Wheeler, H.A., "Transmission-Line Properties of a Round Wire in a Polygon Shield," IEEE Transactions on Microwave Theory and Techniques, vol. MTT-27, No. 8, pp. 717-721, Aug. 1979.

Office Action dated Dec. 30, 2011 from U.S. Appl. No. 12/442,376, 10 pages.

\* cited by examiner

TRANSMISSION LINE COMPRISED OF A CENTER CONDUCTOR ON A PRINTED CIRCUIT BOARD DISPOSED WITHIN A GROOVE

RELATED APPLICATION INFORMATION

This application claims the benefit under 35 U.S.C. §119 (e) of U.S. Provisional Patent Application Ser. No. 61/037, 986, filed Mar. 19, 2008.

FIELD OF THE INVENTION

The present invention concerns a transmission line. Further, it concerns a method for production of a transmission line.

BACKGROUND ART

The use of microstrip lines with air as the dielectric has been used in base station antennas since at least the mid-90s. The advantage is low loss and ease of manufacture in the sense that a flat ground plane can be used for the lines. The disadvantage of such lines is the necessary width, which for example at a 3 mm separation is 13 mm for a 50 ohms line. The absence of a dielectric, other than air, also means that the mutual coupling is rather high.

As another prior art, in respect of the present invention, U.S. Pat. No. 5,652,557 could be mentioned. This patent discloses a transmission line consisting of a longitudinal groove in a dielectric material having longitudinal walls and bottom disposed with a metallisation film. In the groove, a conductor line is formed by a metal film.

However, the conductor of U.S. Pat. No. 5,652,557 is manufactured by disposing a conductor film on a dielectric. Such a production method can be complex and expensive, yielding an expensive transmission line.

SUMMARY OF THE INVENTION

It is an object of the present invention to propose a solution for or a reduction of the problems of prior art. A main object is consequently to propose a transmission line having beneficial electric properties and at the same time is both improved in construction and easy to employ.

According to one aspect of the invention this is accomplished by a transmission line. Using a center conductor comprising at least one conductor formed on a side of a printed circuit board (PCB) provides for a simple and relatively inexpensive construction. Another proposition could be to use a piece of metal as the center conductor. However, compared to such a piece of metal, a PCB offers prospects of better dimensional accuracy, lower weight, and possibly also lower cost than sheet metal.

According to another aspect of the invention, one or more of the above objectives is achieved with a method for production of a transmission line. This is a straightforward method of production that is simple to employ.

BRIEF DESCRIPTION OF THE DRAWINGS

Embodiments exemplifying the invention will now be described, by means of the appended drawings, in which.

DETAILED DESCRIPTION OF THE INVENTION

Figure 1A:
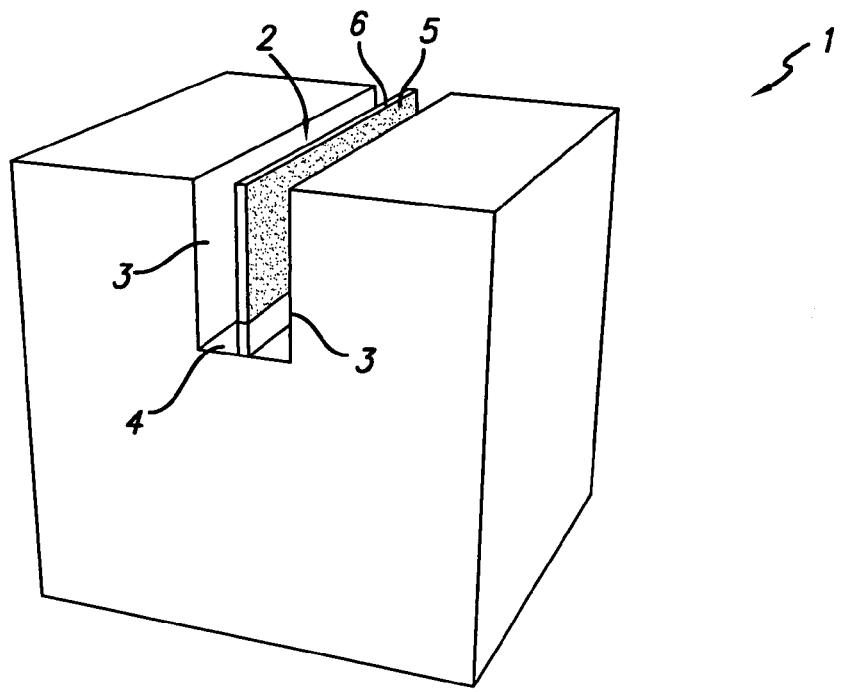
FIGS. 1a and 1b illustrate schematically a transmission line of the invention.

A conceptual embodiment of the invention is shown in FIG. 1a. It is a transmission line 1 that comprises:
 a groove 2 defined by two parallel conducting walls 3 and a conducting floor 4 all electrically connected to each other, together forming a peripheral conductor of the transmission line, and
 a center conductor 5, at least partly submersed in the groove 2, the center conductor 5 being isolated from the conducting walls 3 and the conducting floor 4 of the groove 2. The center conductor 5 comprises at least one conductor formed on a side of a printed circuit board 6. The transmission line 1 is operating in near transverse electromagnetic mode (TEM-mode) or quasi TEM-mode. The small discrepancy from a full TEM-mode is due to the different permittivity of air and the dielectric material in the thin PCB dielectric surrounding the center conductor.

Typically, such a conductor formed on a side of a printed circuit board would be a conducting strip formed on the printed circuit board. However, other conductors are, in theory, not ruled out; it is conceivable to have other types of conductors than strips formed on the printed circuit board.

The design of the transmission line as in FIG. 1a ensures efficient use of the conducting strip area, since the field is distributed on both sides of the strip due to the surrounding walls and floor of the groove. This means a lower loss compared to a microstrip transmission line. At the same time the open configuration brought about by the groove provides for good accessibility of the line during assembly while still affording mechanical protection of the center conductor. The production of such a transmission line could be configured to be easy and relatively inexpensive.

An alternative to the PCB would be to use a piece of sheet metal. However, compared to such a solution, the PCB may provide better dimensional accuracy, lower weight, and possibly also lower cost than such a piece of sheet metal.

Figure 1B:
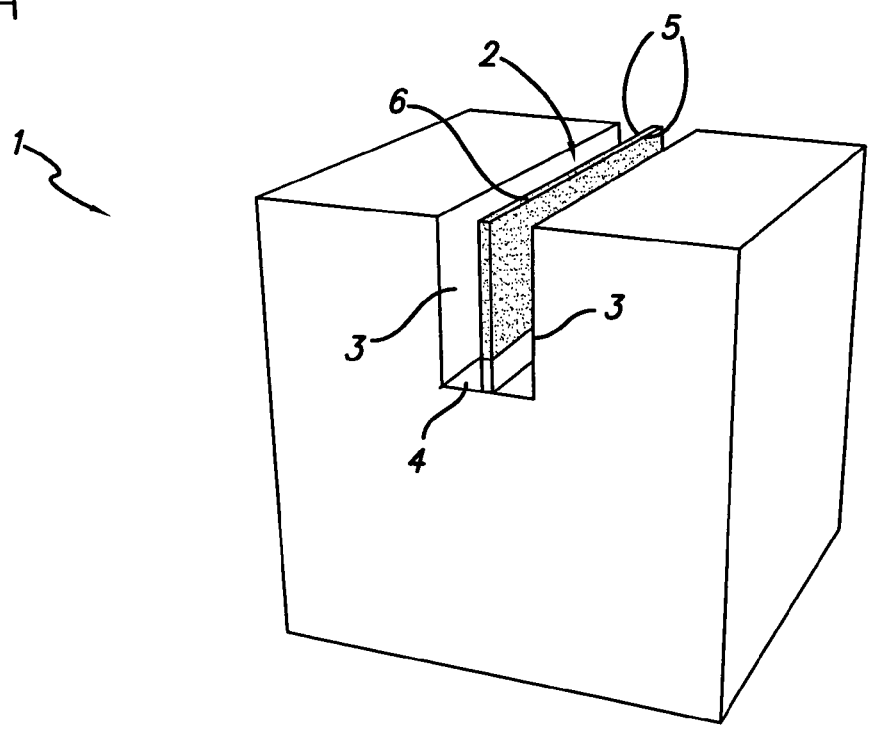

In FIG. 1b a transmission line 1 is shown having a similar structure to that of FIG. 1a with corresponding structural elements 2, 3, 4 as described above, wherein the center conductor 5 comprises two conductors on two sides of the printed circuit board 6, i.e. both sides of the PCB are used for the center conductor. This solution provides for a slightly lower impedance over a frequency range from 0.50-2.0 GHz according to simulations, see below.

Figure 2A:
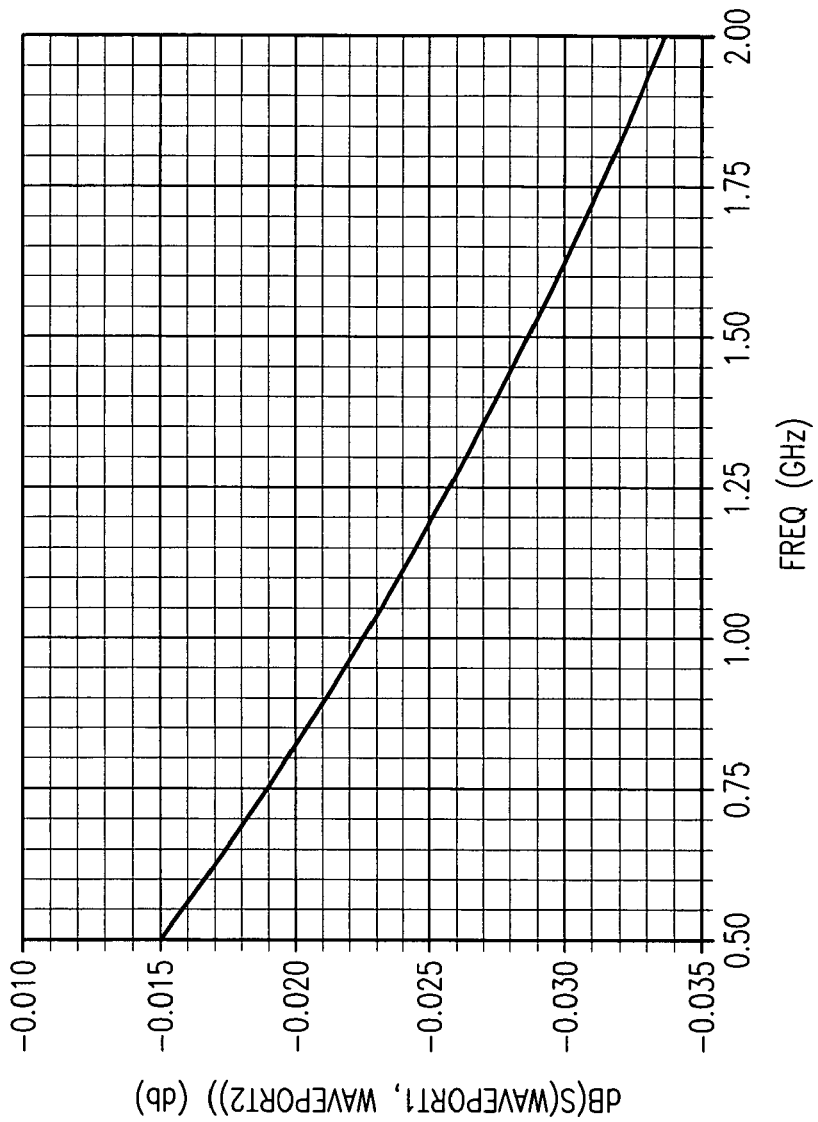
FIGS. 2a and 2b illustrate schematically a case of attenuation properties for the transmission lines of FIGS. 1a and 1b.
Figure 2B:
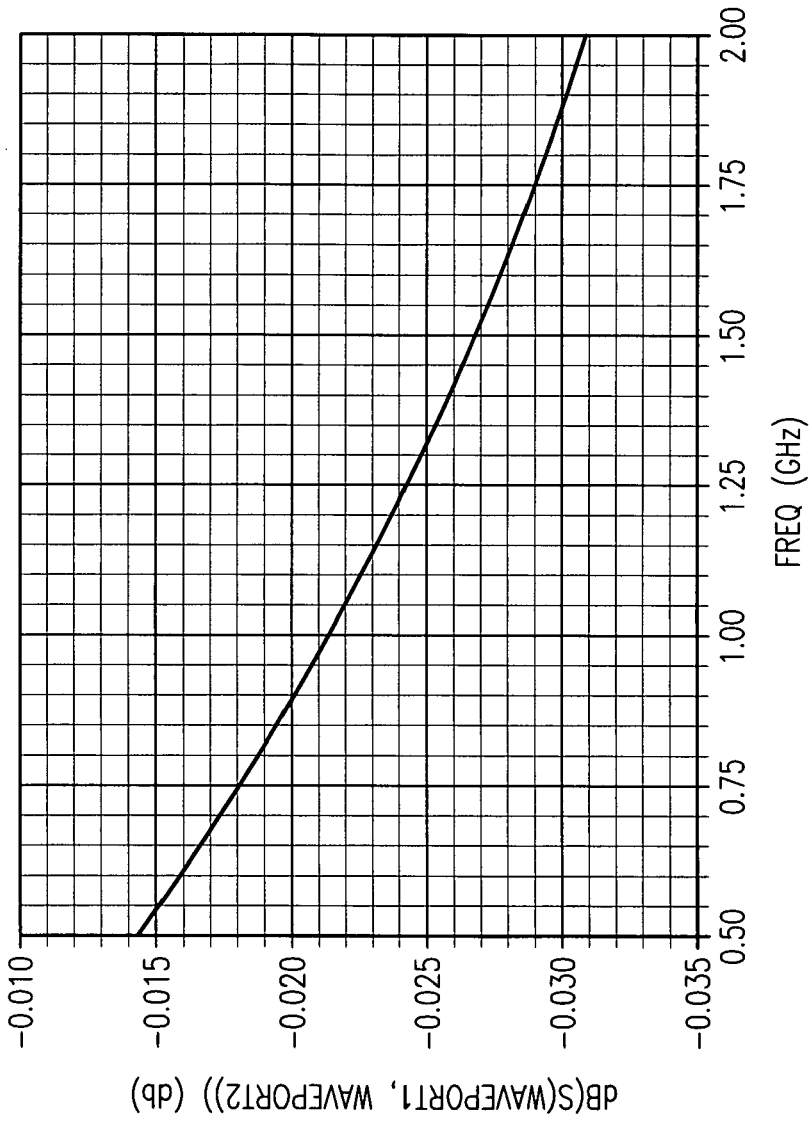

Simulations of the attenuation of the transmission lines in FIGS. 1a and 1b respectively are shown in FIGS. 2a and 2b. FIG. 2a corresponds to FIG. 1a and FIG. 2b corresponds to FIG. 1b. FIGS. 1a/2a are for a one-sided, 200 mm copper line on a 20 mil (0.508 mm) thick Rogers 4003 substrate. FIGS. 1b/2b are for a two-sided, 200 mm copper line on a 20 mil (0.508 mm) thick Rogers 4003 substrate. FIGS. 2a and 2b show attenuation vs. frequency between two ports (waveport 1, waveport 2). For both cases, total width of the groove 2 was 8 mm (corresponding to the floor 4), depth was 15 mm (corresponding to the walls 3). Material of walls and floor was aluminium. Line width was 11 mm, line thickness was 35 μm. As can be seen, attenuation is a bit less for the two-sided case of FIGS. 1b/2b.

Returning to FIGS. 1a and 1b for awhile, the center conductor 5 of the transmission line 1, could be formed on the printed circuit board 6 by etching. This means that a high dimensional precision of the center conductor could be accomplished. Such precision could be attained using standard, and therefore inexpensive, etching equipment well known in the electronics industry.

In principle, the printed circuit board 6 of the transmission line 1 could be positioned in the groove 2 with its main surfaces perpendicular to the walls 3 of the groove 2. However, when the printed circuit board 6 of the transmission line 1 is positioned in the groove 2 with its main surfaces in parallel with the walls 3 of the groove 2, a more efficient use of the conducting strip area is achieved, resulting in a lower attenuation of the transmission line.

Figure 3:
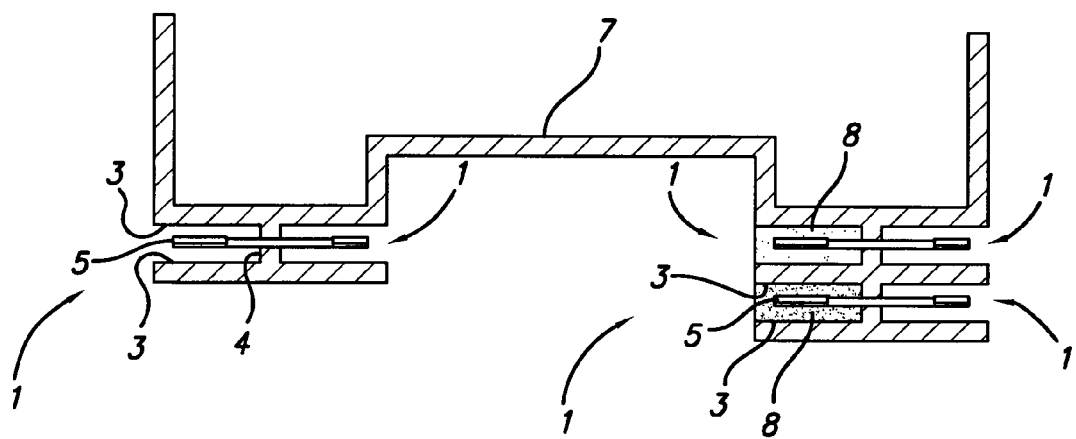
FIG. 3 illustrates transmission lines according to the invention mounted on the back of an antenna reflector.

The walls 3 and the floor 4 of the transmission line 1 according to the invention could be constructed in many different ways. They could be separate parts that are joined together by suitable means or an integral part. Such separate parts or integral part could for instance be an aluminium part, such as an aluminium extrusion. Also, as seen in FIG. 3, at least a part of any of the walls 3 and the floor 4 defining the groove could also be a part of an antenna reflector 7. This enables a rational construction wherein e.g. the back of an antenna reflector can be reused as a part of the groove, thus providing a dual function. FIG. 3 illustrates in a side elevation view an antenna reflector having mounted at the back of it a plurality of transmission lines 1. Also shown in FIG. 3 is a slidable dielectric 8 positioned in a space between the center conductor 5 and at least one of the parallel conducting walls 3. Due to the slidable dielectric, the impedance of a part of the transmission line could be controlled, for instance in order to vary/tune the phase of a signal on the transmission line. The dielectric could be slidable in a suitable direction. In FIG. 3 that could be in the direction in or out of the paper. Alternatively it could be in a direction in or out of the groove, i.e. left or right in the figure.

Figure 4A:
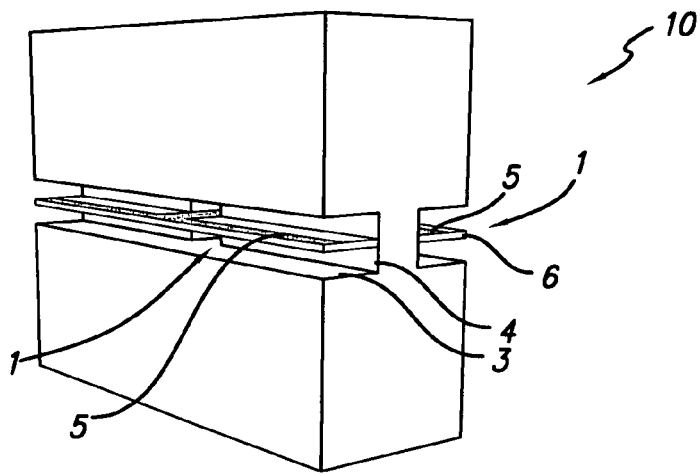
FIGS. 4a-4c illustrate two transmission lines according to the invention, connected to each other with a conducting element, from different perspectives, FIG. 5 illustrate a dielectric in an embodiment of the invention.
Figure 4B:
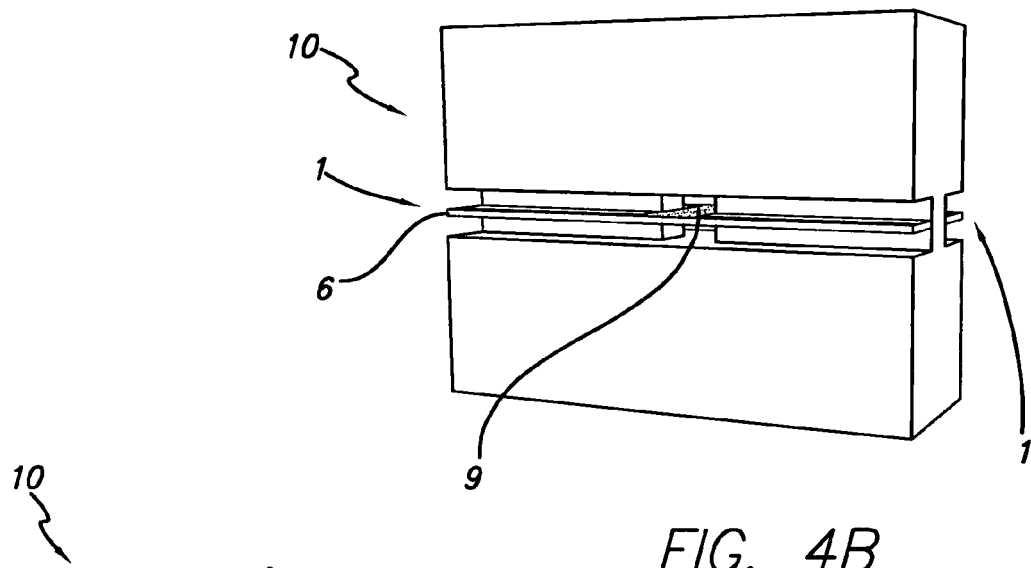
Figure 4C:
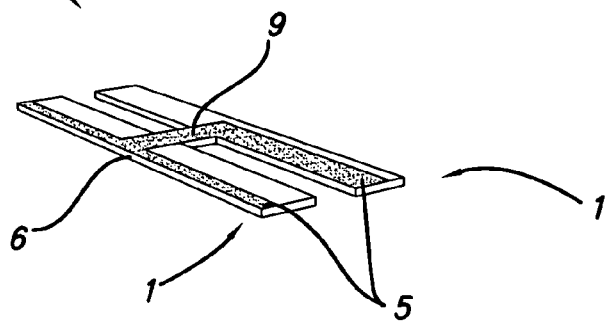

As FIGS. 4a-4c show, a System 10 comprising a plurality of transmission lines 1 according to any of the previously described transmission lines of the invention could be formed, wherein at least two center conductors 5 (FIGS. 4a, 4c) of the plurality of transmission lines are connected to each other with a conducting element 9 (FIGS. 4b, 4c) in order to provide for a dividing of a signal that can enter the system 10 on one of the plurality of transmission lines into at least one other transmission line. The conducting element 9 is shown in FIG. 4a-4c going through a port between the two grooves of the figure.

FIGS. 4a-4c all show the same system 10 from different angles and in the case of FIG. 4c, also in some translucency in order to clarify the design and placement of a PCB 6 with its center conductor 5 in the system.

In order to provide for a rational and economical production of such a system 10, at least two center conductors could be formed on a same printed circuit board 6. That would yield at least two conductors using only one PCB, as can be seen in FIGS. 4a-4c. The forming of at least two center conductors on the same PCB also has the further benefit that the conducting element 9 between them could be a conductor formed on the printed circuit board 6. In that way, there would not be any requirements for the soldering of wires between the transmission lines.

Figure 5:
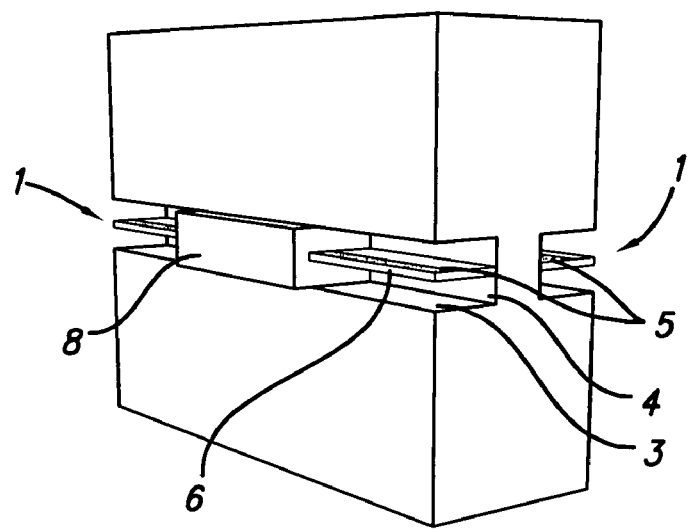

A figure similar to that of FIGS. 4a-4c is shown in FIG. 5 with the addition of a slidable dielectric 8. This is basically a three dimensional schematic view of the slidable dielectric of FIG. 3, showing only two transmission lines 1 though.

Figure 6:
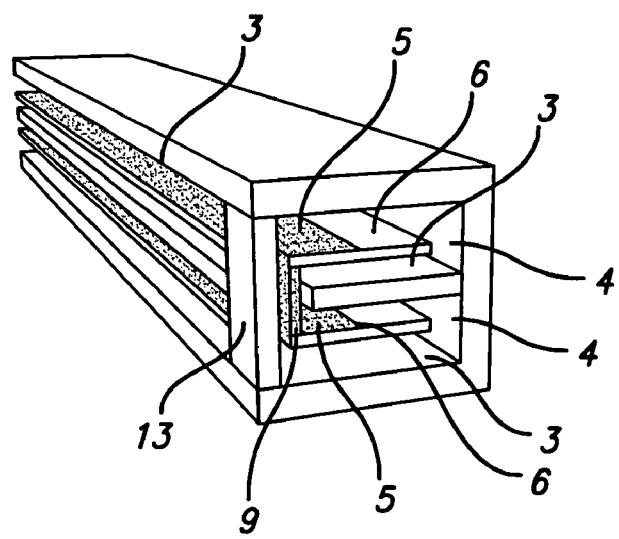
FIG. 6 illustrates the use of a cross connection between two separate transmission lines.

With reference to FIG. 6, for the case wherein at least two center conductors 5 in the system of the invention are on separate printed circuit boards 6, it would be beneficial if the conducting element 9 extends through one of the walls 3 and the floor 4, that is either through one of the walls or through the floor, of the groove of at least one of the transmission lines, preferably both of the lines. This is shown in FIG. 6, where a cut out in the middle wall is effected in order to provide space for the conducting element 9. It should be noted that the walls and floors of the at least two transmission lines should share the same voltage potential, in order to avoid any differential modes. In particular, it is important to maintain the same potential of the walls in both transmission lines. It can be seen in FIG. 6 that the two center conductors 5 are connected with a conducting element 9. Further, in order to maintain the same potential of the walls in both transmission lines, a conductor 13 is provided connecting both (outer) walls 3.

Figure 7A:
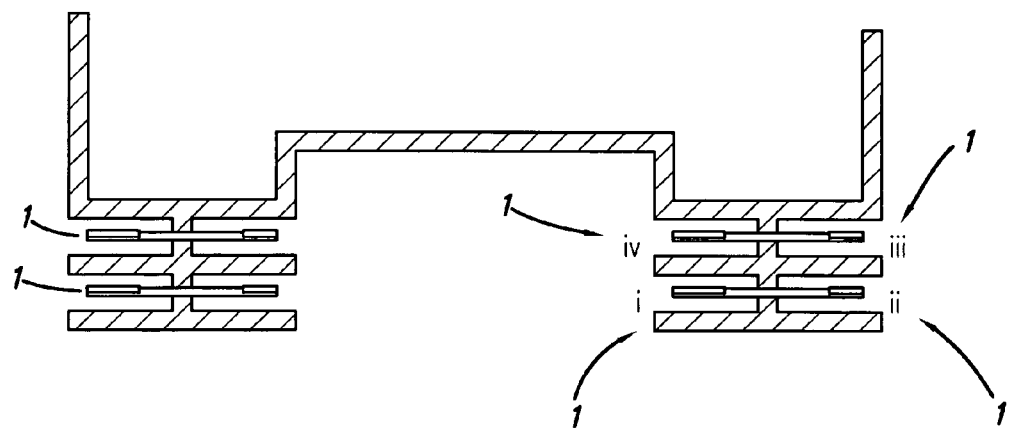
FIGS. 7a-7b illustrate the use of a plurality of transmission lines of the invention.
Figure 7B:
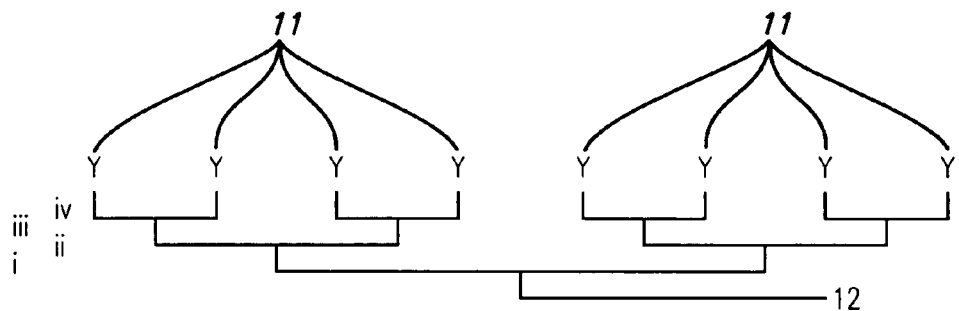

A system 10 as has been described above can, as an example, be put to use as an antenna feed, feeding antenna elements with signals. Thus, such a system could replace the usual coaxial cables in such an application. This could simply be accomplished by having a system of at least two transmission lines according to the invention connected to a corresponding at least two antenna elements 11. (Of course, the use of a singular transmission line of the invention to feed an antenna element is also possible, however that can be thought of as just a singular transmission line rather than a system of transmission lines.) In comparison to a system using coaxial cables, this solution has the prospect of being both inexpensive and allowing for improved production. Such a system in accordance with the invention is depicted in FIGS. 7a and 7b. FIG. 7a shows a system of transmission lines 1 connected to the back of an antenna reflector (no antenna radiating element is shown in FIG. 7a). The different transmission lines 1 in FIG. 7a are connected to each other in a way shown schematically in FIG. 7b. An antenna feed signal can be supplied at the tail 12 in FIG. 7b. This signal is then distributed to the different antenna element pairs 11 by the successive forking of a transmission line into new transmission lines. This can be seen in FIG. 7b; each new fork level (or T-branch level) results in a doubling of the number of branches of the transmission lines. Each level is depicted with a roman numeral (i, ii, iii, iv, respectively) in FIG. 7b and each such corresponding level is indicated in the schematic FIG. 7a. In the end, the transmission lines are connected to an antenna element pair 11, as seen in FIG. 7b.

The invention also comprises a method for production of a transmission line comprising the steps:

a) manufacturing a groove 2 defined by two parallel conducting walls 3 and a conducting floor 4 all electrically connected to each other, together forming a peripheral conductor of the transmission line, and b) submersing the center conductor 5, at least partly in the groove 2, such that the center conductor 5 is isolated from the conducting walls 3 and the conducting floor 4 of the groove 2, distinguished in that in step b: submersing a center conductor 5 that comprises at least one conductor on a side of a printed circuit board 6.

The manufacture of a groove 2 in step a) could be accomplished in many ways. For instance by milling in a solid body such as a metal body. Another alternative would be to create a metal profile by extrusion or folding of a metal sheet. A third alternative would be to connect different separate parts that together form the groove. It should be emphasised that any embodiment of the transmission line and the system described above, could be produced in a corresponding step in the method of the invention.

The invention claimed is:

1. Transmission line comprising:
   a groove defined by two parallel conducting walls and a conducting floor all electrically connected to each other, together defining a peripheral conductor of the transmission line, wherein the groove is open at a side opposite to the conducting floor, and
   a center conductor, at least partly submersed in the groove, the center conductor being isolated from the conducting walls and the conducting floor of the groove, wherein the center conductor comprises at least one conductor formed on at least one side of a printed circuit board, wherein the printed circuit board is positioned in the groove with main surfaces thereof in parallel with the walls of the groove.

2. Transmission line according to claim 1, wherein the at least one conductor comprises two conductors on two sides of the printed circuit board.

3. Transmission line according to claim 1 or 2, wherein the center conductor is formed on the printed circuit board by etching.

4. Transmission line according to claim 1, wherein a slidable dielectric is positioned in a space between the center conductor and at least one of the parallel conducting walls.

5. Transmission line according to claim 1, wherein the groove is defined by an aluminium extrusion.

6. Transmission line according to claim 1, wherein at least a part of any of the walls and the floor defining the groove is a part of an antenna reflector.

7. Method for production of a transmission line comprising the steps:
   a) manufacturing a groove defined by two parallel conducting walls and a conducting floor all electrically connected to each other, together forming a peripheral conductor of the transmission line, wherein the groove is open at a side opposite to the conducting floor, and
   b) inserting a center conductor, at least partly in the groove, such that the center conductor is isolated from the conducting walls and the conducting floor of the groove, wherein said center conductor comprises at least one conductor on a side of a printed circuit board and wherein said inserting step comprises positioning the printed circuit board in the groove with main surfaces thereof in parallel with the walls of the groove.

8. System comprising:
   a plurality of transmission lines each comprising,
      a groove defined by two parallel conducting walls and a conducting floor all electrically connected to each other, together defining a peripheral conductor of the transmission line, wherein the groove is open at a side opposite to the conducting floor, and
      a center conductor, at least partly submersed in the groove, the center conductor being isolated from the conducting walls and the conducting floor of the groove, wherein the center conductor comprises at least one conductor formed on a side of a printed circuit board, wherein the printed circuit board is positioned in the groove with main surfaces thereof in parallel with the walls of the groove;
   wherein at least two of the center conductors of the plurality of transmission lines are connected to each other with a conducting element in order to provide for a dividing of a signal that can enter the system on one of the plurality of transmission lines into at least one other transmission line of the plurality of transmission lines.

9. System according to claim 8, wherein said at least two of the center conductors are disposed on a single printed circuit board.

10. System according to claim 9, wherein the conducting element is a conductor disposed on the single printed circuit board.

11. System according to claim 8, wherein said at least two of the center conductors are on separate printed circuit boards and the conducting element is extending through one of the walls and the floor of the corresponding groove of at least one of the plurality of transmission lines.

12. System according to claim 8, wherein at least two of the plurality of transmission lines are connected to a corresponding at least two antenna elements.

* * * * *